(12) United States Patent
Feng et al.

(10) Patent No.: US 9,072,796 B2
(45) Date of Patent: *Jul. 7, 2015

(54) METHOD FOR PREPARING DEUTERATED DIPHENYLUREA

(71) Applicant: SUZHOU ZELGEN BIOPHARMACEUTICAL CO., LTD., Jiangsu (CN)

(72) Inventors: Weidong Feng, Jiangsu (CN); Xiaoyong Gao, Jiangsu (CN); Xiaojun Dai, Jiangsu (CN)

(73) Assignee: SUZHOU ZELGEN BIOPHARMACEUTICAL CO., LTD., Jiangsu (CN)

(*) Notice: Subject to any disclaimer, the term of this patent is extended or adjusted under 35 U.S.C. 154(b) by 0 days.

This patent is subject to a terminal disclaimer.

(21) Appl. No.: 14/092,253

(22) Filed: Nov. 27, 2013

(65) Prior Publication Data

US 2014/0088311 A1    Mar. 27, 2014

Related U.S. Application Data

(62) Division of application No. 13/635,827, filed as application No. PCT/CN2011/071922 on Mar. 17, 2011, now Pat. No. 8,618,306.

(30) Foreign Application Priority Data

Mar. 18, 2010   (CN) .......................... 2010 1 0127706

(51) Int. Cl.
| | |
|---|---|
| C07D 213/62 | (2006.01) |
| A61K 51/04 | (2006.01) |
| C07D 213/81 | (2006.01) |
| C07C 209/24 | (2006.01) |
| C07D 209/48 | (2006.01) |
| C07D 213/68 | (2006.01) |
| C07B 59/00 | (2006.01) |

(52) U.S. Cl.
CPC .......... *A61K 51/0455* (2013.01); *C07D 213/81* (2013.01); *C07C 209/24* (2013.01); *C07D 209/48* (2013.01); *C07D 213/68* (2013.01); *C07B 59/002* (2013.01)

(58) Field of Classification Search
None
See application file for complete search history.

(56) References Cited

U.S. PATENT DOCUMENTS

| | | | |
|---|---|---|---|
| 8,748,666 B2 * | 6/2014 | Gao et al. ...................... | 564/487 |
| 2009/0069388 A1 | 3/2009 | Czarnik | |
| 2013/0060044 A1 | 3/2013 | Feng et al. | |

FOREIGN PATENT DOCUMENTS

| | | | |
|---|---|---|---|
| CN | 101676266 A | * | 3/2010 |
| WO | 00/42012 | | 7/2000 |
| WO | 2011/113366 A1 | | 9/2011 |

OTHER PUBLICATIONS

International Search Report for PCT/CN2011/071922 mailed Jun. 23, 2011.
English translation of PCT International Preliminary Report on Patentability (Form PCT/IPEA/409) for PCT/CN2011/071922 completion date Jun. 4, 2012.
English translation of PCT Written Opinion of The International Searching Authority (Form PCT/ISA/237 for PCT/CN2011/071922 completion date Jun. 16, 2011.
U. Pleiss et al., "Syntheses of [2H3, 15N], [14C]NexavarTM and its labeled metabolites", Journal of Labelled Compounds and Radiopharmaceuticals, 2006, vol. 49, pp. 603-613.
Scott Wilhelm et al., "BAY 43-9006: Preclinical Data", Current Pharmaceutical Design, 2002, 8, pp. 2225-2257.
CAPLUS 2010 393760.
Chinese Office Action in related application, dated Aug. 8, 2013.
Joseph E. Saavedra, "*Lithiation of α-Nitrosaminoalkyl Ethers. Synthetic Equivalents of α-Primary Amino Carbanions*[1]" J. Org. Chem., 1983, 48, pp. 2388-2392.

* cited by examiner

*Primary Examiner* — Heidi Reese
(74) *Attorney, Agent, or Firm* — Smith, Gambrell & Russell LLP (57) ABSTRACT

Disclosed are an intermediate compound of N-(1,1,1-trideuterated methyl)phthalimide, and its use in the preparation of deuterated diphenylurea derivative.

4 Claims, 2 Drawing Sheets

METHOD FOR PREPARING DEUTERATED DIPHENYLUREA

FIELD OF INVENTION

This invention relates to the field of chemical synthesis, and particularly relates to some intermediates for preparing deuterated diphenylurea and the synthetic methods and the use thereof.

BACKGROUND OF INVENTION

The ω-diphenylurea derivatives are known as the compounds with c-RAF kinase inhibition activity. For example, WO2000/042012 disclosed a class of ω-carboxyl-aryl-substituted diphenylurea and the use thereof for treating cancer and related diseases.

Initially, ω-diphenylurea compounds, such as Sorafenib, were firstly found as the inhibitor of c-RAF kinases. The other studies had shown that they could also inhibit the MEK and ERK signal transduction pathways and activities of tyrosine kinases including vascular endothelial growth factor receptor-2 (VEGFR-2), vascular endothelial growth factor receptor-3 (VEGFR-3), and platelet-derived growth factor receptor-β (PDGFR-β) (Curr Pharm Des 2002, 8, 2255-2257). Therefore, they were called multi-kinase inhibitors that resulted in dual anti-tumor effects.

Sorafenib (trade name Nexavar), a novel oral multi-kinase inhibitor, was developed by Bayer and Onyx. In December 2005, based on its outstanding performance in phase III clinical trials for advanced renal cell carcinoma, Sorafenib was approved by FDA for treating advanced renal cell carcinoma, and marketed in China in November 2006. However, Sorafenib has various side-effects, such as hypertension, weight loss, rash and so on.

However, the current procedure for preparing deuterated diphenylurea compounds is immature, and has some disadvantages, such as high-cost, low-yield, low-purity or difficulties in separation and so on. Therefore, novel and highly efficient procedures for preparing diphenylurea compounds are needed to be developed.

SUMMARY OF INVENTION

The subject of the invention is to provide highly efficient procedures for preparing highly pure diphenylurea compounds and the intermediates therein.

In the first aspect, the invention provides a method for preparing 2-(methyl-$d_3$)isoindoline-1,3-dione, comprising:

(a) in an inert solvent, reacting a alkali metal salt of phthalimide with compound A, $$Z-\overset{O}{\underset{O}{S}}-O-CD_3 \quad (A)$$

wherein, Z is $CH_3$, $O-CD_3$ or

[R-substituted phenyl structure]

wherein R is methyl, nitro or halogen (F, Cl or Br), to form 2-(methyl-$d_3$)isoindoline-1,3-dione:

[phthalimide-N-CD3 structure]

In one embodiment, said inert solvent includes N,N-dimethylformamide (DMF), N,N-dimethylacetamide (DMA), dimethylsulfoxide (DMSO), N-methylpyrrolidone (NMP), tetrahydrofuran, 1,4-dioxane, or the combination thereof.

In one embodiment, in step (a), the reaction temperature is −10° C. to reflux temperature; preferably is −4° C. to 100° C.; and more preferably is 20-80° C.

In one embodiment, the reaction time is 0.1-24 hours; preferably is 0.3-5 hours; and more preferably is 0.5-2 hours.

In one embodiment, in step (a), said alkali metal salt of phthalimide includes (but is not limited to): potassium phthalimide, sodium phthalimide, phthalimide, or the combination thereof.

In one embodiment, in step (a), said compound A includes: methyl-$d_3$ 4-methyl-benzenesulfonate, methyl-$d_3$ 3-nitrobenzenesulfonate, or methyl-$d_3$ 4-nitrobenzenesulfonate.

In one embodiment, prior to step (a) of said method it further includes step (a1):
under a basic condition and in an inert solvent, reacting deuterated methanol with tosyl chloride to form methyl-$d_3$ 4-methyl-benzenesulfonate.

In one embodiment, in step (a1), said inert solvent includes water, tetrahydrofuran, or the mixture thereof.

In the second aspect, the invention provides a method for preparing a salt of (methyl-$d_3$)amine, comprising:
in an inert solvent or an aqueous solvent, reacting 2-(methyl-$d_3$)isoindoline-1,3-dione with an acid to form a salt of (methyl-$d_3$)amine, wherein said acid includes: hydrochloric acid, sulfuric acid, hydrobromic acid, trifluoroacetic acid, or the combination thereof.

In one embodiment, said reaction temperature is 30 to reflux temperature (such as 120° C.), preferably 40-110° C.

In one embodiment, said reaction time is 0.5-48 hours, preferably is 1-36 hours, and more preferably is 2-24 hours.

In the third aspect, the invention provides an intermediate used for preparing deuterated diphenylurea, wherein the intermediate is 2-(methyl-$d_3$)isoindoline-1,3-dione.

In one embodiment, the intermediate is used for preparing deuterated diphenylurea or as the raw material for preparing deuterated diphenylurea.

In one embodiment, said deuterated diphenylurea is compound I:

(I)

[Structure of compound I with substituents $R^1, R^2, R^3, R^4, R^5, R^6, R^7, R^8, R^9, R^{10}, R^{11}, R^{12}, R^{13}, R^{14}$ and X]

wherein,

X is N or N⁺—O⁻;

R¹ is halogen (such as F, Cl or Br), one or more deuterium-substituted or perdeuterated C1-C4 alkyl;

R² is non-deuterated C1-C4 alkyl, one or more deuterium-substituted or perdeuterated C1-C4 alkyl, or partly or totally halogen-substituted C1-C4 alkyl;

each of R³, R⁴, R⁵, R⁸, R⁹, R¹⁰, R¹², R¹³, and R¹⁴ is independently hydrogen, deuterium, or halogen (such as F, Cl or Br);

R⁶ is hydrogen, deuterium, or one or more deuterium-substituted or perdeuterated C1-C4 alkyl;

R⁷ is hydrogen, deuterium, or one or more deuterium-substituted or perdeuterated C1-C4 alkyl; and provided that at least one of R², R³, R⁴, R⁵, R⁶, R⁷, R⁸, R⁹, R¹⁰, R¹¹, R¹², R¹³ or R¹⁴ is deuterated or is deuterium.

More preferably, said deuterated diphenylurea is selected from 4-(4-(3-(4-chloro-3-(trifluoromethyl)phenyl]ureido)-phenoxy)-N-(methyl-d₃) picolinamide(CM4307);

4-(4-(3 -(4-chloro-3-(trifluoromethyl)phenyl]ureido)-phenoxy)-N-(methyl-d₃) picolinamide p-toluenesulfonate (CM4307•TsOH);

4-(4-(3-(4-chloro-3-(trifluoromethyl)phenyl]ureido)-3-fluorophenoxy)-N-(methyl-d₃)picolinamide (CM4309);

4-(4-(3-(4-chloro-3-(trifluoromethyl)phenyl]ureido)-3-fluorophenoxyl)-N-(methyl-d₃)picolinamide p-toluenesulfonate (CM4309•TsOH);

It should be understood that in the present invention, any of the technical features specifically described above and below (such as in the Examples) can be combined with each other, thereby constituting new or preferred technical solutions that are not described one by one in the specification.

DETAILED DESCRIPTION OF INVENTION

After studies, the inventors unexpectedly discovered that, compared with the un-deuterated compound, the deuterated ω-diphenylurea of the invention and the pharmaceutically acceptable salts thereof possessed better pharmacokinetic and/or pharmacodynamic properties. Therefore, they were much more suitable as raf kinase inhibitors for preparing medicaments to treat cancer and the relevant diseases.

Furthermore, the inventors also discovered that diphenylurea compound can be more efficiently and easily prepared by using the new intermediate 2-(methyl-d₃)isoindoline-1,3-dione. Based on this discovery, the inventors completed the present invention.

Definition

As used herein, the term "halogen" refers to F, Cl, Br and I. Preferably, halogen is selected from F, Cl, and Br.

As used herein, the term "alkyl" refers to straight-chain or branched chain alkyl, Preferably, alkyl is C1-C4 alkyl, such as methyl, ethyl, propyl, iso-propyl, butyl, iso-butyl, tert-butyl and so on.

As used herein, the term "deuterated" means that one or more hydrogens of compounds or groups are substituted by deuteriums. "Deuterated" can be mono-substituted, bi-substituted, multi-substituted or total-substituted. The terms "one or more deuterium-substituted" and "substituted by deuterium once or more times" can be used interchangeably.

In one embodiment, the deuterium content in a deuterium-substituted position is at least greater than the natural abundance of deuterium (0.015%), preferably >50%, more preferably >75%, more preferably >95%, more preferably >97%, more preferably >99%, more preferably >99.5%.

In one embodiment, the compound of formula (I) comprises at least one deuterium atom, preferably three deuterium atoms, and more preferably five deuterium atoms.

As used herein, the term "compound CM4306" is 4-(4-(3-(4-chloro-3-(trifluoromethyl)phenyl]ureido)-phenoxy)-N-methylpicolinamide.

As used herein, the term "compound CM4307" is 4-(4-(3-(4-chloro-3-(trifluoromethyl)phenyl]ureido)-phenoxy)-N-(methyl-d₃)picolinamide.

As used herein, the term "compound CM4308" is 4-(4-(3-(4-chloro-3-(trifluoromethyl)phenyl]ureido)-3-fluorophenoxy)-N-methylpicolinamide.

As used herein, the term "compound CM4309" is 4-(4-(3-(4-chloro-3-(trifluoromethyl)phenyl]ureido)-3-fluorophenoxy)-N-(methyl-d₃)picolinamide.

As used herein, the term "TsOH" represents p-toluenesulfonic acid. Therefore, CM4307•TsOH represents the p-toluenesulfonate of CM4307. CM4309•TsOH represents the p-toluenesulfonate of CM4309.

Deuterium-Substituted ω-diphenylurea

The preferred deuterated ω-diphenylurea compounds of the invention have the structure of formula I:

(I)

wherein,

X is N or N⁺—O⁻;

R¹ is halogen (such as F, Cl or Br), one or more deuterium-substituted or perdeuterated C1-C4 alkyl;

R² is non-deuterated C1-C4 alkyl, one or more deuterium-substituted or perdeuterated C1-C4 alkyl, or partly or totally halogen-substituted C1-C4 alkyl;

each of R³, R⁴, R⁵, R⁸, R⁹, R¹⁰, R¹¹, R¹², R¹³ and R¹⁴ is independently hydrogen, deuterium, or halogen (such as F, Cl or Br);

R⁶ is hydrogen, deuterium, or one or more deuterium-substituted or perdeuterated C1-C4 alkyl;

R⁷ is hydrogen, deuterium, or one or more deuterium-substituted or perdeuterated C1-C4 alkyl; and provided that at least one of R², R³, R⁴, R⁵, R⁶, R⁷, R⁸, R⁹, R¹⁰, R¹¹, R¹², R¹³ or R¹⁴ is deuterated or is deuterium.

In one embodiment, the deuterium content at a deuterium-substituted position is at least greater than the natural abundance of deuterium (0.015%), preferably >30%, more preferably >50%, more preferably >75%, or >95%, or >99%.

In one embodiment, except for H, all or almost all (>99wt %) of the elements (such as N, C, O, F, etc.) of compound (I) are naturally existing elements with highest abundance, such as $^{14}N$, $^{12}C$, $^{16}O$ and $^{19}F$.

In one embodiment, compounds of formula (I) at least contain one deuterium atom, preferably three deuterium atoms, and more preferably five deuterium atoms.

In one embodiment, $R^1$ is halogen, preferably chlorine.

In one embodiment, $R^2$ is trifluoromethyl,

In one embodiment, $R^6$ or $R^7$ is independently selected from hydrogen, deuterium, deuterated methyl, or deuterated ethyl; preferably, mono-deuterated methyl, bi-deuterated methyl, tri-deuterated methyl, mono-deuterated ethyl, bi-deuterated ethyl, tri deuterated ethyl, tetra-deuterated ethyl, or penta-deuterated ethyl.

In one embodiment, $R^6$ or $R^7$ is independently selected from hydrogen, methyl or tri-deuterated methyl.

In one embodiment, $R^3$, $R^4$ or $R^5$ is independently selected from hydrogen or deuterium.

In one embodiment, $R^8$, $R^9$, $R^{10}$ or $R^{11}$ is independently selected from hydrogen or deuterium.

In one embodiment, $R^{12}$, $R^{13}$ or $R^{14}$ is independently selected from hydrogen or deuterium.

In one embodiment, said compounds are selected from:

N-(4-chloro-3-(trifluoromethyl)phenyl)-N'-(4-(2-(N-(methyl-d$_3$)aminoformyl)-4-pyridyloxy)phenyl)urea (or 4-(4-(3-(4-chloro-3-(trifluoromethyl)phenyl]ureido)-phenoxy)-N-(methyl-d$_3$)picolinamide);

4-(4-(3-(4-chloro-3-(trifluoromethyl)phenyl)ureido)phenoxy)-2-(N-(methyl-d$_3$)aminoformyl)pyridine-1-oxide;

N-(4-chloro-3-(trifluoromethyl)phenyl)-N'-(2,6-d$_2$-4-(2-(N-(methyl-d$_3$)aminoformyl)-4-pyridyloxy)phenyl)urea;

N-(4-chloro-3-(trifluoromethyl)phenyl)-N'-(4-(2-d-6-(N-(methyl-d$_3$)aminoformyl)-4-pyridyloxy)phenyl)urea;

or N-(4-chloro-3-(methyl-d$_3$)phenyl)-N'-(4-(2-(N-(methyl-d3)aminoformyl)-4-pyridyloxy)phenyl)urea.

or 4-(4-(3-(4-chloro-3-(trifluoromethyl)phenyl]ureido)-3-fluoro-phenoxyl)-N-(methyl-d$_3$)picolinamide.

Intermediate

As used herein, the term "the intermediate of the invention" is 2-(methyl-d$_3$)isoindoline-1,3-dione (or N-(methyl-d$_3$)benzosuccinimide);

Such intermediate can be called as "deuterated methyl phthalimide".

Except for H, all or almost all (>99 wt %) of the elements (such as N, C, O, etc.) of the above compounds are naturally existing elements with highest abundance, such as $^{14}N$, $^{12}C$ and $^{16}O$.

Preparation

The preparation methods of the intermediates of the invention and compound (I) are described in detail as below. However, these specific methods are not provided for the limitation of the invention. The compounds of the invention can be readily prepared by optionally combining any of the various methods described in the specification or various methods known in the art, and such combination can be readily carried out by the skilled in the art.

The method for preparing un-deuterated ω-diphenylurea and the physiologically compatible salts thereof used in the invention is known. The deuterated ω-diphenylurea can be prepared in the same route using the corresponding deuterated compounds as starting materials. For example, compound (I) can be prepared according to the method described in WO2000/042012, except that the deuterated material is used instead of un-deuterated material in the reaction.

In general, during the preparation, each reaction is conducted in an inert solvent, at a temperature between room temperature to reflux temperature (such as 0-80° C., preferably 0-50° C.). Generally, the reaction time is 0.1-60 hours, preferably, 0.5-48 hours.

Taking CM4307 as an example, an optimized preparation route is shown as follows:

Moreover, CM4309 can be prepared using the above route with 3-fluoro-4-aminophenol instead of compound 4.

The deuterium can be introduced by using deuterated methylamine.

Deuterated methylamine or the hydrochloride thereof can be prepared through the following reactions. Deuterated nitromethane is obtained by reacting nitromethane with deuterium water in the presence of base (such as sodium hydride, potassium hydride, deuterated sodium hydroxide, deuterated potassium hydroxide, potassium carbonate and the like) or phase-transfer catalyst. If necessary, the above experiment can be repeated to produce high-purity deuterated nitromethane. Deuterated nitromethane is reduced in the presence of zinc powder, magnesium powder, iron, or nickel and the like to form deuterated methylamine or the hydrochloride thereof.

Furthermore, deuterated methylamine or the hydrochloride thereof can be obtained through the following reactions.

The key intermediate 3 can be synthesized from deuterated methanol ($CD_3OD$) through the following reactions.

The detailed preparation procedure is described in Example 1.

The main advantages of the present invention include:

(1) High-purity 2-(methyl-$d_3$)isoindoline-1,3-dione can be efficiently prepared by the optimized process, which will be of benefit to the subsequent reactions.

(2) Various of deuterated diphenylurea can be conveniently and high efficiently prepared by using the intermediate of the invention.

(3) The reaction conditions are milder and the operating process is safer.

The present invention will be further illustrated below with references to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, parts and percentage are calculated by weight.

PREPARATION EXAMPLE 1 FOR THE INTERMEDIATE (1) Preparation of the Intermediate 2-(methyl-$d_3$)isoindoline-1,3-dione

1. Preparation of Methyl-$d_3$ p-toluenesulfonate

Sodium hydroxide (180 g, 4.5 mol, 5.0 eq) was added into water (288 mL). Methanol-$d_3$ (32.4 g, 900 mmol, 1.0 eq) was added at 0° C., and a solution of tosyl chloride (206 g, 1.1 mmol, 1.2 eq) in tetrahydrofuran (288 mL) was slowly added dropwise. The mixture was warmed to room temperature and stirred overnight. The mixture was neutralized h dropwise adding acetic acid (206 g) below 25° C. The reaction mixture was filtered and separated. The aqueous phase was extracted with ethyl acetate (100 mL). The filter cake was dissolved in water (300 mL) and extracted with ethyl acetate (200 mL). The organic phases were combined, washed with saturated sodium carbonate (100 mL) and saturated brine (100 mL), dried over anhydrous sodium sulfate and filtered. The solvent in the filtrate was removed under reduced pressure to afford the title compound (160.5 g, purity 99%, yield 94%) as a pale yellow liquid.

$^1$H NMR (CDCl$_3$, 400 MHz): δ 3.20 (s, 3H), 7.71-7.75(m, 2H), 7.84-7.88(m, 2H).

2. Preparation of 2-(methyl-$d_3$)isoindoline4,3-dione

To N,N-dimethyl formamide (DMF, 225 mL), potassium phthalimide (166.7 g, 0.9 mol, 2.0 eq) was added. Methyl-$d_3$ p-toluenesulfonate (85.2 g, 0.45 mmol, 1.0 eq) prepared in the previous step was added dropwise at room temperature. The mixture was stirred at 60° C. for 0.5 hour, and filtered immediately. The filter cake was washed with DMF (250 mL and 100 mL) for two times. The DMF solutions were combined, and water (1150 mL) was added dropwise at 0° C. to precipitate a white solid. The solid was filtered and washed with water (100 mL×2). The obtained solid was dried under vacuum to give the title compound (64 g, purity 99.6%, yield 85%) as a white solid.

$^1$H NMR(CDCl$_3$, 400 MHz): δ 7.71-7.77(m, 2H), 7.84-7.88(m, 2H).

3. Preparation of (methyl-$d_3$)amine hydrochloride

To a solution of distilled water (625 mL) and concentrated hydrochloric acid (625 mL., 7.5 mol, 15 eq), 2-(methyl-$d_3$) isoindoline-1,3-dione (82 g, 0.5 mol, 1 eq) was added at room temperature. The mixture was heated to 105° C. and refluxed overnight. The mixture was cooled to room temperature, filtered, and washed with distilled water (50 mL×2). Hydrochloric acid was removed under reduced pressure to afford a light yellow solid. Anhydrous ethanol (140 mL) was added, and the resulted mixture was refluxed for 1 hour. The mixture was cooled to room temperature, and filtered. The solid was washed with ethanol (30 mL) and dried under vacuum to give the title compound (28 g, yield 80%) as a white solid.

$^1$H NMR(DMSO-$d_6$, 400 MHz): δ 8.05(br, 2H).

PREPARATION EXAMPLE 2 FOR THE INTERMEDIATE

Preparation of the Intermediate 2-(methyl-$d_3$)isoindoline-1,3-dione

1: Preparation for 2-(methyl-$d_3$)isoindoline-1,3-dione

Step 2 in preparation example 1 was repeated except that: potassium phthalimide was replaced by phthalimide (5.9 g, 40 mmol, 2.0 eq), and potassium hydroxide (80%, 1.2 g, 40 mmol, 2.0 eq) was added in batches at 0° C. After stirred for 30 min, a solution of methyl-$d_3$ p-toluenesulfonate (3.8 g, 20 mmol, 1.0 eq) in DMF (10 mL) was added dropwise. After the addition, the mixture was heated to 60° C. and stirred for 30 min. Conducting the filtration, washing and drying under vacuum by the same method as step 2 of preparation example 1 to give the title compound (2.1 g, purity 81%, yield about 62%) as a white solid.

PREPARATION EXAMPLE 3 FOR THE INTERMEDIATE

1: Preparation of 2-(methyl-d₃)isoindoline-1,3-dione

Step 2 in preparation example 1 was repeated except that: potassium phthalimide is replaced by phthalimide (5.9 g, 40 mmol, 2.0 eq), and sodium hydride (80%, 1.2 g, 40 mmol, 2.0 eq) was added in batches at 0° C. After stirred for 30 min, a solution of methyl-d₃ p-toluenesulfonate (3.8 g, 20 mmol, 1.0 eq) is DMF (10 mL) was added dropwise. After the addition, the mixture was heated to 60° C. and stirred for 30 min. Conducting the filtration, washing and drying in vacuum by the same method as step 2 of preparation example 1 to give the title compound (2.7 g, purity 86%, yield about 80%) as a white solid.

The above experiments showed that the new intermediate 2-(methyl-d₃)isoindoline-1,3-dione could be prepared through the three methods above. However, compared with the procedure by using phthalimide and potassium hydroxide or sodium hydride, using potassium phthalimide as an intermediate, on one hand, higher purity 2-(methyl-d₃)isoindoline-1,3-dione could be obtained more efficiently, which was of benefit to the following reactions, on the other hand, the reaction condition is milder and the operation is safer because of without using sodium hydride.

In Step 3 of preparation example 1 for the intermediate, because the highly pure 2-(methyl-d₃)isoindoline-1,3-dione was used, high-purity N-(methyl-d₃)amine hydrochloride (purity>99.5%) was obtained.

EXAMPLE 1

N-(4-chloro-3-(trifluoromethyl)phenyl)-N'-(4-(2-(N-(methyl-d3)aminoformyl)-4-pyridyloxy)phenyl)urea (Compound CM4307)

Route:

Scheme 1

1. Preparation of 4-chloro-N-(methyl-d₃)picolinamide (3)

Into a 250 mL single-neck round-bottom flask equipped with waste gas treatment device, thionyl chloride (60 mL) was added. Anhydrous DMF (2 mL) was dropwise added slowly while keeping temperature at 40-50° C. After the addition, the mixture was stirred for 10 min, and then nicotinic acid (20 g, 162.6 mmol) was added in portions in 20 min. The color of the solution gradually changed from green into light purple. The reaction mixture was heated to 72° C., and refluxed for 16 hours with agitation. A great amount of solid precipitate formed. The mixture was cooled to room temperature, diluted with toluene (100 mL) and concentrated to almost dry. The residue was diluted with toluene and concentrated to dry. The residue was filtered and washed with toluene to give 4-chloropicolinoyl chloride as a light yellow solid. The solid was slowly added into a saturated solution of (methyl-d₃)amine in tetrahydrofuran in an ice-bath. The mixture was kept below 5° C., and stirred for 5 hours. The mixture was concentrated and ethyl acetate was added to give a white solid precipitate. The mixture was filtered, and the filtrate was washed with saturated brine, dried over sodium sulfate and concentrated to give 4-chloro-N-(methyl-d₃)picolinamide (3) (20.68 g, 73% yield) as a light yellow solid.

$^1$H NMR (CDCl₃, 300 MHz): 8.37 (d, 1H), 8.13 (s, 1H), 7.96(br, 1H), 7.37(d, 1H).

2. Preparation of 4-(4-aminophenoxy)-N-(methyl-d₃) picolinamide (5)

To dry DMF (100 mL), 4-aminophenol (9.54 g, 0.087 mol) and potassium tert-butoxide (10.3 g, 0.092 mol) were added in turn. The color of the solution turned into deep brown. After stirring at room temperature for 2 hours, 4-chloro-N-(methyl-d₃)picolinamide (3) (13.68 g, 0.079 mol) and anhydrous potassium carbonate (6.5 g, 0.0467 mol) were added. The reaction mixture was heated to 80° C. and stirred overnight. TLC detection showed the reaction was complete. The reaction mixture was cooled to room temperature, and poured into a solution of ethyl acetate (150 mL) and saturated brine (150 mL). The mixture was stirred and stood for separation. The aqueous phase was extracted with ethyl acetate (3×100 mL). The extracted layers were combined, washed with saturated brine (3×100 mL), dried over anhydrous sodium sulfate, and concentrated to afford 4-(4-aminophenoxy)-N-(methyl-d₃) picolinamide (18.00 g, 92% yield) as a light yellow solid.

$^1$H NMR (CDCl₃, 300 MHz): 8.32 (d, 1H), 7.99 (br, 1H), 7.66 (s, 1H), 6.91-6.85 (m, 3H), 6.69 (m, 2H), 3.70 (br, s, 2H).

3. Preparation of N-(4-chloro-3-(trifluoromethyl) phenyl)-N'-(4-(2-(N-(methyl-d₃)amino formyl)-4-pyridyloxy)phenyl)urea (CM4307)

To methylene chloride (120 mL), 4-chloro-3-trifluoromethyl-phenylamine (15.39 g, 78.69 mmol) and N,N'-carbonyldiimidazole (13.55 g, 83.6 mmol) were added. After stirred at room temperature for 16 hours, a solution of 4-(4-aminophenoxy)-N-(methyl-d₃)picolinamide (18 g, 73 mmol) in methylene chloride (180 mL) was slowly added dropwise and the mixture was stirred at room temperature for another 18 hours. TLC detection showed the reaction was complete. The mixture was concentrated to about 100 mL by removing methylene chloride through a rotary evaporator and stood for several hours at room temperature. A great amount of white solid precipitated. The mixture was filtered and the solid was washed with abundant methylene chloride. The filtrate was concentrated by removing part of solvent, and sonic solids precipitated again. Two parts of the solid were combined and washed with abundant methylene chloride to afford N-(4-chloro-3-(trifluoromethyl)phenyl)-N'-(4-(2-(N-(methyl-d₃) aminoformyl)-4-pyridyloxy)phenyl)urea (CM4307, 20.04 g, 58% yield) as a white powder (pure product).

$^1$H MAR (CD₃OD, 300 MHz): 8.48 (d, 1H), 8.00 (d, 1H), 7.55 (m, 5H), 7.12 (d, 1H), 7.08 (s, 2H), ESI-HRMS m/z: C₂₁H₁₃D₃ClF₃N₄O₃, Calcd. 467.11, Found 490.07 (M±Na)⁺.

Furthermore, Compound CM4307 was dissolved in methylene chloride and reacted with m-chloroperoxybenzoic acid to afford the oxidized derivative: 4-(4-(3-(4-chloro-3-(trifluoromethyl)phenyl)ureido)phenoxy)-2-(N-(methyl-d₃)aminoformyl)pyridine-1-oxide.

EXAMPLE 2

Preparation of 4-chloro-N-(methyl-d₃)picolinamide (3)

a) Phthalimide (14.7 g, 0.1 mol), deuterated methanol (3.78 g, 0.105 mol, 1.05 eq) and triphenylphosphine (28.8 g, 0.11 mol, 1.1 eq) were dissolved in anhydrous tetrahydrofuran. A solution of DEAD (1.1 eq) in tetrahydrofuran was dropwise added under the ice-bath. After addition, the mixture was stirred for 1 hour at room temperature. The mixture was purified by chromatography column, or the solvent in the mixture was removed, and then to the residue was added an appropriate amount of DCM and cooled in the refrigerator to precipitate the solid. The mixture was filtered and the filtrate was concentrated by a rotary evaporator, and then the residue was purified by flash chromatography column to afford the pure product of 2-(N-(methyl-d₃))-isoindole-1,3-dione (14.8 g, 90% yield).

Although the intermediate could be prepared through the above procedure, the purity of the product was low. It needed to be purified by column chromatography to get the pure product. The work-ups were complicated, and the reagents (such as triphenylphosphine and diethyl azodicarboxylate (DEAD), etc.) were environmentally unfriendly. Therefore, it was not suitable for industrial production.

b) 2-(N-(methyl-d₃))-isoindole-1,3-dione (12.5 g, 0.077 mol) was dissolved in a suitable amount of hydrochloric acid (6 N, 50 mL) and the mixture was refluxed for 24-30 hours in a sealed tube. The reaction mixture was cooled to room temperature and then cooled below 0° C. in the refrigerator to precipitate the solid. The mixture was filtered and the solid was washed with the cold deionized water. The filtrate was collected and concentrated by a rotary evaporator to remove water. The resulted solid was dried to afford (methyl-d₃) amine hydrochloride. Anhydrous DCM (100 mL) was added in (methyl-d₃)amine hydrochloride and methyl 4-chloropicolinate hydrochloride (6.52 g, 0.038 mol, 0.5 eq) and sodium carbonate (12.2 g, 0.12 mol, 1.5 eq) were added. The reaction flask was sealed and placed in the refrigerator for one day. After TLC detection showed the reaction was complete, the reaction mixture was washed with water, dried, concentrated and purified by chromatography column to afford 4-chloro-N-(methyl-d₃)picolinamide (compound (3), 5.67 g, 86% yield). The structural feature of the compound was the same as that in Example 1.

EXAMPLE 3

Preparation of diphenylurea Compound CM4307 from 2-(N-(methyl-d₃))-isoindole-1,3-dione $^1$H NMR(DMSO-d$_6$, 400 MHz): δ 7.64(dd, J=2 Hz, 5.2 Hz, 1H), 7.97(d, J=1.6 Hz, 1H), 8.54(d, J=5.2 Hz, 1H), 8.74(br, 1H).
MS (ESI, m/z) calcd. for C$_7$H$_4$D$_3$ClN$_2$O: 173, found: 174 [M+H]$^+$ 2: Preparation of 4-(4-aminophenoxy)-N-(methyl-d₃) picolinamide A3

Under nitrogen, 4-chloro-N-(methyl-d₃)picolinamide (2.4 g, 13.8 mmol, 1 eq) was dissolved in dimethylsulfoxide (10 mL). To the resulted solution, 4-aminophenyol (1.6 g, 14.9 mmol, 1.08 eq) was added followed by addition of potassium 1: Preparation of 4-chloro-N-(methyl-d₃)picolinamide A2

To a three-necked bottom flask with tetrahydrofuran (250 mL), methyl 4-chloro-2-picolinate (50 g, 291 mmol, 1 eq) was added. N-(methyl-d₃)amine hydrochloride (31 g, 437 mmol, 1.5 eq) and anhydrous potassium carbonate(400-mesh, 80 g, 583 mmol, 2 eq) were added with stirring. After the mixture was stirred at room temperature for 20 h, water (250 mL) and methyl tert-butyl ether (150 mL) were added. The mixture was stirred and separated. The aqueous layer was extracted with methyl tert-butyl ether (100 mL). The organic phases were combined, dried over anhydrous sodium sulfate and filtered. The solvent in the filtrate was removed under reduced pressure to obtain the product (48 g, purity 99%, yield 96%) as light yellow liquid.

tert-butoxide (1.7 g, 15.2 mmol, 1.1 eq) in batches. After the inner temperature was stable, the inner temperature was raised and kept at 80° C. for 4 hours. After the inner temperature was cooled to room temperature, iso-propanol (10 mL) was added with stirring to dilute the reaction mixture. Under nitrogen, concentrated hydrochloric acid (37%, 10 mL) was added dropwise, and the mixture was stirred for 1 h, and then filtrated. The resulted solid was dissolved in water (20 mL), activated carbon (0.1 g) was added. The resulted mixture was stirred for 1 h and filtered. A solution of potassium carbonate (2 g potassium carbonate dissolved in 6 mL water) was slowly added dropwise into the filtrate and some solids formed. The mixture was filtered, and the solid was washed with water (5 mL), and dried in vacuum to give the title product (2.7 g, purity 99.9%, yield 78%) as a light brown crystal.

$^1$H NMR(DMSO-d$_6$, 400 MHz): δ 5.19(br, 2H), 6.66-6.68 (m, 2H), 6.86-6.88(m, 2H), 7.07(dd, J=2.8 Hz, 5.6 Hz, 1H), 7.36(d, J=2.8 Hz, 1H), 8.45(d, J=5.6 Hz, 1H), 8.72(br, 1H).

MS (ESI, m/z) calcd. for C$_{13}$H$_{10}$D$_3$N$_3$O$_2$Cl: 246, found: 247[M+H]$^+$ 3. Preparation of 4-(4-(3-(4-chloro-3-(trifluoromethyl)phenyl]ureido)-phenoxy)-N-(methyl-d$_3$)picolinamide (CM4307)

Under nitrogen, 4-(4-aminophenoxy)-N-(methyl-d$_3$)picolinamide (2.6 g, 10.6 mmol, 1 eq) was dissolved in dichloromethane (10 mL) and dimethylsulfoxide (3 mL). A solution of 1-chloro-4-isocyanato-2-(trifluoromethyl)benzene (2.50 g, 11.1 mol, 1.05 eq) in dichloromethane (8 mL) was slowly added dropwise to the above solution at room temperature. The resulted mixture was stirred for 20 min. The mixture was cooled to 2° C. and water (10 mL) was added dropwise. The resulted mixture was stirred for 0.5 h and filtered. The product was washed with dichloromethane (10 mL). The resulted product was dried in vacuum to give an off-white solid (4.7 g, purity 99.8%, yield 95.4%).

$^1$H NMR (DMSO-d$_6$, 400 MHz): δ 7.15(dd, J=2.8 Hz, 5.6 Hz, 1H), 7.17-7.19(m,2H), 7.40(d, J=2.4 Hz, 1H), 7.59-7.69 (m, 4H), 8.13(d, J=2.4 Hz, 1H), 8.51(d, J=6 Hz, 1H), 8.75(br, 1H), 8.90(br, 1H), 9.22(br, 1H),

MS (ESI, m/z) calcd. for C$_{21}$H$_{13}$D$_3$ClF$_3$N$_4$O$_3$: 467, found: 468[M+H]$^+$

EXAMPLE 4

Preparation of 4-(4-(3-(4-chloro-3-(trifluoromethyl)phenyl]ureido)-phenoxy)-N-(methyl-d$_3$)picolinamide p-toluenesulfonate (CM4307·TsOH)

p-toluenesulfonic acid monohydrate (1.6 g, 8.5 mmol, 0.88 eq) was dissolved in anhydrous ethanol (5 mL). The resulted solution was filtered, and then heated to 70° C. and kept at the same temperature. 4-(4-(3-(4-chloro-3-(trifluoromethyl)phenyl]ureido)-phenoxy)-2-(N-(methyl-d$_3$))picolinamide (4.5 g, 9.6 mol, 1 eq) and p-toluenesulfonic acid monohydrate (0.66 g, 3.5 mmol, 0.36 eq) were suspended in ethanol (50 mL). The mixture was heated to 78° C. and refluxed for 40 min till the solid was fully dissolved. The resulted solution was slightly cooled and filtered when the solution was warm. The filtrate was heated till the inner temperature was 78° C. and refluxed for 1 h till the solution was clear. The pre-prepared ethanol solution of p-toluenesulfonic acid monohydrate at 70° C. was quickly added in one time. Heating was stopped and the mixture was cooled freely, stirred for 0.5 h at 0° C. and filtered. The product was washed with anhydrous ethanol (5 mL×2), dried in vacuum at 50° C. for 24 h to give a white to off-white solid (5.8 g, purity 99.3%, yield 93%).

$^1$H NMR (DMSO-d$_6$, 400 MHz): δ 2.30(s, 3H), 7.15(d, J=8.8 Hz, 2H), 7.20(d, J=8.8 Hz, 2H), 7.23(dd, J=2.8 Hz, 6 Hz, 1H), 7.52(d, J=8 Hz, 2H), 7.55(d, J=2.8 Hz, 1H), 7.63(d, J=8.8 Hz, 3H), 7.68(dd, J=2.4 Hz, 9.2 Hz, 1H), 8.03(br, 1H), 8.14(d, J=2.4 Hz, 1H), 8.56(d, J=6 Hz, 1H), 8.91(br, 1H), 9.17(br, 1H), 9.36(br, 1H).

$^{13}$C NMR(DMSO-d$_6$, 400 MHz): δ 21.1, 26.1, 111.7, 115.2, 117.0, 120.7(2C), 121.6 (2C), 121.9, 122.8, 123.2, 124.6, 125.6 (2C), 127.2, 129.0(2C), 132.3, 138.8, 139.5, 139.9, 144.1, 146.6, 147.2, 152.8, 159.9, 170.7 ppm.

Liquid chromatography condition: Agilent 1100 Series; chromatographic column; Synergi 4μ POLAR-RP 80A, 250×4.6 mm, 4 μm; column temperature: 25° C.; detection wavelength: UV 210 nm; mobile phase: A: ammonium dihydrogen phosphate 10 B: methanol; injection volume: 10 μL; flow rate: 0.8 mL/min; run time: 70 min; gradient: 50% mobile phase B from 0 to 15 min, mobile phase B being increased to 75% from 15 to 32 min, then 75% mobile phase B eluting for 23 min from 32 to 55 min. retention time: 4.95 min (p-toluenesulfonic acid); 47.11 min (CM4307).

EXAMPLE 5

Preparation of diphenylurea Compound CM4309 from 2-(N-(methyl-d$_3$))-isoindole-1,3-dione 1: Preparation of 4-chloro-pyridyl-2-(N-(methyl-d$_3$)) amide A2

The preparation method was identical to Example 3.

2: Preparation of 4-(4-amino-3-fluorophenoxy)-N-(methyl-d$_3$)picolinamide B1

Potassium tert-butoxide (15 g, 130 mmol, 1.3 eq) was suspended in N,N-dimethylacetylamide (DMA, 50 mL). A solution of 4-amino-3-fluorophenol (16 g, 127 mmol, 1,3 eq) in DMA(50 mL) was slowly added dropwise at 0-5° C. The resulted mixture was stirred at room temperature for 20 min. The mixture was heated to 100C. A solution of 4-chloro-N-(methyl-d$_3$)picolinamide 3 (17 g, 97 mmol, 1 eq) in DMA (50 mL) was slowly added dropwise. After the addition, the mixture was stirred for 0.5 h, then cooled to room temperature, diluted with ethyl acetate (1.5 L) and stirred for 0.5 h. Then the mixture was filtered to remove the inorganic salts. The filtrate was washed with water (500 mL×3), dried over anhydrous sodium sulfate and concentrated under reduced pressure to remove the solvents. To the resulted crude product was added ethanol (100 mL). The resulted mixture was refluxed for 2 h, then cooled to room temperature and filtered to give a brown solid (20 g, HPLC purity 96%, yield 80%).

$^1$H NMR(CD$_3$OD, 400 MHz): δ 6.74-6.77(m, 1H), 6.87 (dd, J=2.4Hz, 11.6 Hz, 1H), 6.93(t, J=10 Hz, 1H), 7.02(dd, J=2.8 Hz, 6 Hz, 1H), 7.54(d, J=2.4 Hz, 1H), 8.44(d, J=6 Hz, 1H).

MS (ESI, m/z) calcd. for C$_{13}$H$_9$D$_3$ClN$_3$O$_2$: 264, found: 265 [M+H]$^+$

3. Preparation of 4-(4-(3-(4-chloro-3-(trifluoromethyl)phenyl]ureido)-3-fluorophenoxy)-N-(methyl-d$_3$)picolinamide (CM4309)

At room temperature, 1-chloro-4-isocyanato-2-(trifluoromethyl)benzene (13 g, 58 mmol, 1.1 eq) was added into a single-necked bottom flask with dichloromethane (70 mL). A solution of 4-(4-amino-3-fluorophenoxy)-N-(methyl-d$_3$)picolinamide (14 g, 53 mmol, 1 eq) in dichloromethane (350 mL) was slowly added dropwise to the above solution. The resulted mixture was stirred at room temperature for 20 h. After the reaction was complete, the mixture was filtered and the solid was washed with dichloromethane (20 mL×2) to obtain a light brown solid (13 g, purity 98%, yield 50%).

$^1$H NMR(DMSO-d$_6$, 400 MHz); δ 7.06-7.10(m, 1H), 7.19 (dd, J=2.4 Hz, 5.6 Hz, 1H), 7.35(dd, J=2.8 Hz, 12 Hz, 1H), 7.43(d, J=2.4 Hz, 1H), 7.63(m, 2H), 8.14(br, 1H), 8.17(t, J=8.8 Hz, 1H), 8.53(d, J=5.6 Hz, 1H), 8.75(d, J=1.6 Hz, 1H), 8.78(br, 1H), 9.54(br, 1H).

MS (ESI, m/z) calcd. for C$_{21}$H$_{12}$D$_3$ClF$_4$N$_4$O$_3$:485, found: 486 [M+H]$^+$

EXAMPLE 6

Preparation of 4-(4-(3-(4-chloro-3-(trifluoromethyl) phenyl)ureido)-3-fluorophenoxy)-N-(methyl-d$_3$) picolinamide p-toluenesulfonate (CM4309•TsOH)

4-(4-(3-(4-chloro-3-(trifluoromethyl)phenyl]ureido)-3-fluorophenoxy)-N-(methyl-d$_3$)picolinamide (2.16 g, 4.33 mmol, 1 eq) was suspended in ethanol (50 mL), and the mixture was refluxed till the solution was clear. The mixture was filtered when it was hot to remove the undissolved materials. The filtrate was refluxed till it was clear, and then p-toluenesulfonic acid (70%, 8.66 mmol, 1 mL, 2 eq) was quickly added in one time. The clear solution was kept for about 0.5 min. The oil bath was turned off and the solution was cooled to room temperature freely. The mixture was stirred for 1 h and filtered. The resulted undissolved materials were dried in vacuum at 50° C., for 20 h to give a white crystal (2.36 g, yield 83%).

$^1$H NMR(DMSO-d$_6$, 400 MHz): δ 2.30(s, 3H), 7.09-7.14 (m, 3H), 7.24(dd, J=2.4 Hz, 5.2 Hz, 1H), 7.37(dd, 2.4 Hz, 11.6 Hz, 1H), 7.48-7.50(m, 3H), 7.61-7.66(m, 2H), 8.15-8.19(m, 2H), 8.56(d, J=5.6 Hz, 1H), 8.79(br, 1H), 8.85(br, 1H), 9.56 (br, 1H), 10.38(br, 1H).

Melting point: 240.7° C.~241° C.

EXAMPLE 7

Preparation of N-(4-chloro-3-(trifluoromethyl)phenyl)-N'-(2,6-d$_2$-4-(2-(N-methyl-d$_3$)aminoformyl)-4-pyridyloxy)phenyl)urea The preparation method was identical with example 1, except that the title compound was obtained using 3,5-d$_2$-4-aminophenol instead of p-aminophenol.

EXAMPLE 8

Preparation of N-(4-chloro-3-(trifluoromethyl)phenyl)-N'-(4-(2-d-6-(N-(methyl-d$_3$)aminoformyl)-4-pyridyloxy)phenyl)urea The preparation method was identical with example 1, except that the title compound was obtained using 2-d-6-carboxylpyridine instead of nicotinic acid.

EXAMPLE 9

Preparation of N-(4-chloro-3-(methyl-d$_3$)phenyl)-N'-(4-(2-(N-(methyl-d$_3$) aminoformyl)-4-pyridyloxy) phenyl)urea The preparation method was identical with example 1, except that the title compound was obtained using 5-amino-2-chloro-(methyl-d$_3$)-benzene instead of 5-amino-2-chloro-trifluorobenzene.

EXAMPLE 10

Pharmacokinetic Evaluation of Deuterated diphenylurea Compounds in Rats 8 male Sprague-Dawley rats, 7-8 weeks-old and body weight about 210 g, were divided into two groups, 4 in each group (rat No.: control group was 13-16; experimental group was 9-12). The rats were orally administrated at a single dose of 3 mg/kg of (a) the undeuterated compound N-(4-chloro-3-(trifluoromethyl)phenyl)-N'-(4-(2-(N-methyl-aminoformyl)-4-pyridyloxy)phenyl)urea (control compound CM4306) or (b) N-(4-chloro-3-(trifluoromethyl)phenyl)-N'-(4-(2-(N-(methyl-d$_3$)-aminoformyl)-4-pyridyloxy)phenyl) urea (Compound CM4307 of the invention) prepared in Example 1. The pharmacokinetic differences of CM4306 and CM4307 were compared.

The rats were fed with the standard feed, given water and chlordiazepoxide. Chlordiazepoxide was stopped at the last night before experiment, and given again two hours after the administration of the compound. The rats were fasted for 16 hours before the test. The compound was dissolved in 30% PEG400. The time for collecting orbital blood was 0.083, 0.25, 0.5, 1, 2, 4, 6, 8 and 24 hours after administrating the compound.

The rats were anaesthetized briefly by inhaling ether. A 300 μL orbital blood sample was collected into the tubes containing a 30 μL 1% heparin saline solution. The tubes were dried overnight at 60° C. before being used. After the blood samples were sequentially collected, the rats were anaesthetized by ether and sacrificed.

After the blood samples were collected, the tubes were gently reversed at least five times immediately to mix the contents sufficiently, and placed on the ice. The blood samples were centrifuged at 4° C. at 5000 rpm for 5 minutes to separate the serum and red blood cells. 100 μL serum was removed to a clean plastic centrifugal tube by pipettor, and the name of the compound and time point was labeled on the tube. Serum was stored at −80° C. before LC-MS analysis.

Figure 1:
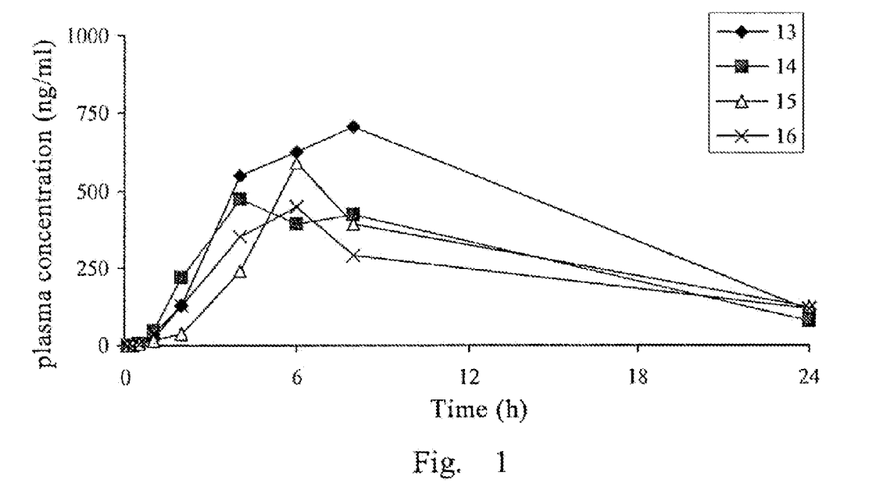
FIG. 1 shows the curves of drug concentration (ng/ml) in plasma after oral administration of 3 mg/kg of the control compound CM4306 to the male SD rats.
Figure 2:
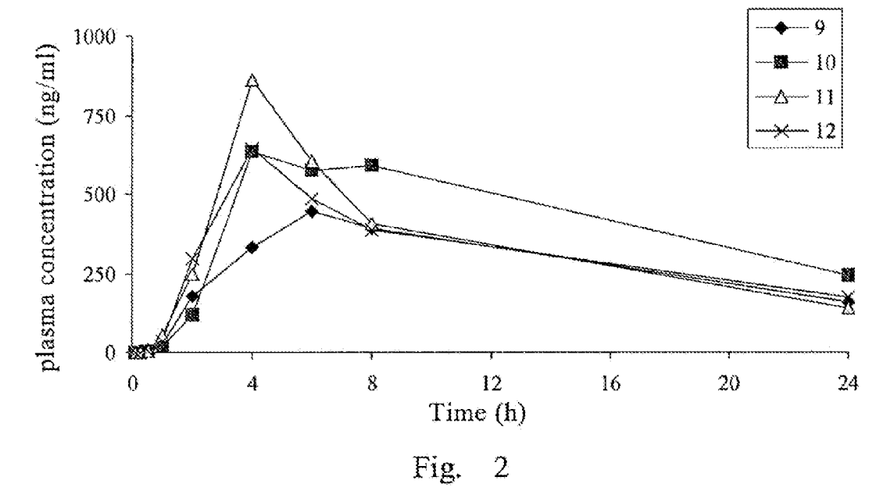
FIG. 2 shows the curves of drug concentration (ng/ml) in plasma after oral administration 3 mg/kg of the compound CM4307 of the invention to the male SD rats.

The results were shown in FIGS. 1-2. The results showed that, compared with CM4306, the half-life ($T_{1/2}$) of CM4307 was longer [11.3±2.1 hours for CM4307 and 8.6±1.4 hours for CM4306, respectively], area under the curve ($AUC_{0-\infty}$) of CM4307 was significantly increased [11255±2472 ng·h/mL for CM4307 and 7328±336 ng·h/mL for CM4306, respectively], and apparent clearance of CM4307 was reduced [275±52 mL/h/kg for CM4307 and 410±18.7 mL/h/kg for CM4306, respectively].

The above results showed that, the compound of the present invention had better pharmacokinetics properties in the animal, and thus had better pharmacodynamics and therapeutic effects.

In addition, the metabolism for the compound of the present invention in organism was changed through deuteration. In particular, the hydroxylation of phenyl became more difficult, which led to the reduction of first-pass effect. In such cases, the dose can be changed, long-acting preparations can be formed, and the applicability can be improved by using long-acting preparations.

Furthermore, the pharmacokinetics was also changed through deuteration. Since another hydrate film is fully formed by deuterated compounds, the distribution of deuterated compounds in organisms is significantly different from that of the non-deuterated compounds.

EXAMPLE 11

The Pharmacodynamics Evaluation of CM4307 for Inhibiting Tumor Growth of Human Hepatocellular Carcinoma SMMC-7721 in Nude Mice Xenograft Model 70 Barb/c nu/nu nude mice, 6 weeks-old, female, were bought from Shanghai Experimental Animal Resource Center (Shanghai B&K Universal Group Limited).

SMMC-7721 cells were commercially available from Shanghai Institutes for Biological Science, GAS (Shanghai, China).

The establishment of tumor nude mice xenograft model: SMMC-7721 cells in logarithmic growth period were obtained. After cell number counting, the cells were suspended in 1×PBS, and the concentration of the cell suspension was adjusted to $1.5 \times 10^7$/ml. The tumor cells were inoculated under the skin of right armpit of nude mice with a 1 ml syringe, $3 \times 10^6/0.2$ ml/mice. 70 nude mice were inoculated in total.

When the tumor size reached 30-130 mm³, 58 mice were divided randomly into different groups. The difference of the mean value of tumor in each group was less than 10%, and drugs were started to be administrated.

The test doses for each group were listed in the following table.

Animal body weight and tumor size were tested twice a week during the experiment. Clinical symptoms were recorded every day. At the end of the administration, the tumor size was recorded by taking pictures. One mouse was sacrificed in each group and tumor tissue was taken and fixed in 4% paraformaidehyde. Observation was continued after the administration, and when the mean size of tumor was larger than 2000 mm³, or the dying status appeared, the animals were sacrificed, gross anatomy was conducted, and the tumor tissue was taken and fixed in 4% paraformaldehyde.

The formula for calculating the tumor volume (TV) is: $TV = a \times b^2/2$, wherein a, b independently represent the length and the breadth of the tumor. The formula for calculating the relative tumor volume (RTV) is: $RTV = Vt/V_0$, wherein $V_0$ is the tumor volume at the beginning of the administration, and Vt is the tumor weight when measured. The index for evaluating the antitumor activity is relative tumor increment rate T/C (%), and the formula is: $T/C\ (\%) = (T_{RTV}/C_{RTV}) \times 100\%$, wherein, $T_{RTV}$ is the RTV of the treatment group, and $C_{RTV}$ is the RTV of the negative control group.

Evaluation standard for efficacy: it is effective if the relative tumor increment rate T/C (%) is <40% and p<0.05 by statistics analysis.

Figure 3:
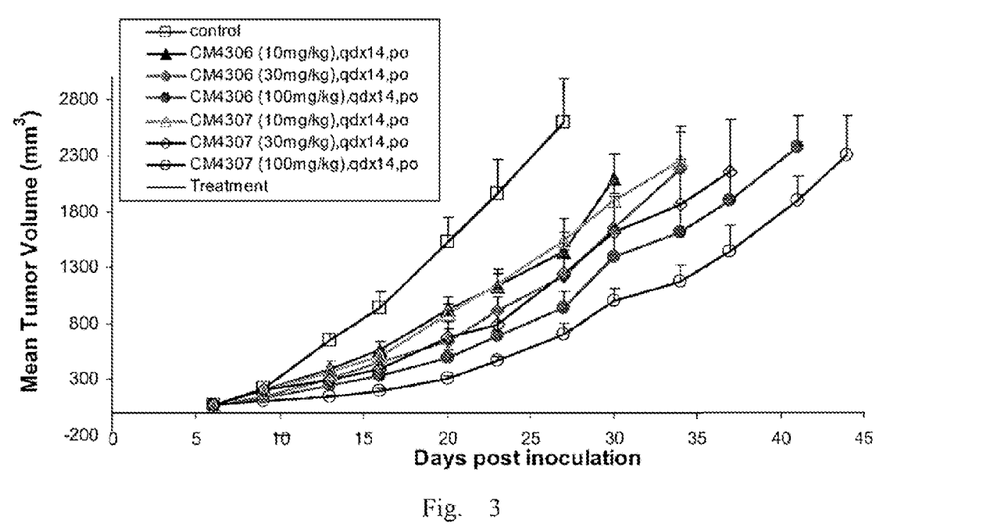
FIG. 3 shows the curves of inhibition efficacy of CM4306 and CM4307 in nude mice xenograft model inoculated with human liver cancer cell SMMC-7721. In this figure, "treatment" means that the treating period was 14 days, followed by the observation period after administration was stopped. The five days before treatment was the period for preparing animal models.

The results were shown in FIG. 3. CM4306 and CM4307 were intragastric administrated every day for 2 weeks at doses of 10, 30, 100 mg/kg, and both compounds showed the dose-dependent effect of the inhibition of tumor growth. At the end of administration, T/C % of CM4306 was 56.9%, 40.6% and 32.2%, respectively. T/C % of CM4307 was 53.6%, 40.8% and 19.6%. T/C % for 100 mg/kg dose groups was <40%, and tumor volume was significantly different (p<0.01) from the control group, indicating the significant effect in inhibiting tumor growth.

Compared with CM4306, the inhibitory efficacy of tumor growth at dosing 100 mg/kg of CM4307 was stronger (the T/C % for CM4307 and CM4306 is 19.6% and 32.2%, respectively, at day 15), there was significant difference in tumor volume between groups (p<0.01). Compared with CM4306, the absolute value of tumor inhibition rate for CM4307 increased more than 10%, the relative value increased about 60% (32.2%/19.6%−1=64%), and CM4307 showed more significant effect for inhibiting tumor growth.

In addition, during the experiment, no other drug-relevant toxic effects were observed.

EXAMPLE 12

The Activity for Inhibiting c-Kit, PDGFR-β Protein Tyrosine Kinase at the Molecular Level 1. Method The activity of diphenylurea compounds for inhibiting c-Kit, PDCFR-β protein tyrosine kinase on molecular level was tested by Enzyme-Linked immunosorbent Assay (ELISA).

Compounds to be tested: CM4306, CM4308 and CM4309.

| Group | Animal | Compounds | Administration | Dose (mg/kg) | Method |
|---|---|---|---|---|---|
| 1 | 10 | control (solvent) | po | 0.1 ml/10 g BW | qd × 2 weeks |
| 2 | 8 | CM4306 | po | 10 mg/kg | qd × 2 weeks |
| 3 | 8 | CM4306 | po | 30 mg/kg | qd × 2 weeks |
| 4 | 8 | CM4306 | po | 100 mg/kg | qd × 2 weeks |
| 5 | 8 | CM4307 | po | 10 mg/kg | qd × 2 weeks |
| 6 | 8 | CM4307 | po | 30 mg/kg | qd × 2 weeks |
| 7 | 8 | CM4307 | po | 100 mg/kg | qd × 2 weeks |

Main Reagents:

Reaction substrate Poly(Glu,Tyr)$_{4:1}$ was bought from Sigma. Monoclonal antibody against tyrosine phosphate PY99 was bought from Santa Cruz. Horseradish peroxidase labeled sheep-against-rat IgG was bought from Calbiochem; ATP, DTT, OPD were bought from Amresco; microplates were bought from Corning; Su11248 was bought from Merk.

The testing method:

See Roskoski, R., Jr. Sunitinib: a VEGF and PDGF receptor protein kinase and angiogenesis inhibitor. Biochem Biophys Res Commun, 356: 323-328, 2007. The details comprise:

Kinase reaction substrate Poly(Glu,Tyr)$_{4:1}$ was diluted to 20 µg/ml by potassium-free PBS, and the microplates were coated. Diphenylurea samples to be tested were added in the wells of the coated microplates (the samples to be tested were made from the stock solution $10^{-2}$ M in DMSO, and diluted to the desired concentration with reaction buffer before use, the resulted solution Was added into the wells to get the final concentration of $10^{-5}$ mol/L in 100 µL reaction system). At the same time, the positive control compound Su11248 was added into the positive control wells.

ATP solution diluted with reaction buffer (the final concentration of ATP is 5 µM) followed by addition of tyrosine kinase diluted with reaction buffer. The total volume of reaction system was 100 µL. At the same time, the negative control wells and the control wells without enzyme were set up.

The reaction system was placed in a wet box, and shaked for 1 h at 37° C. shielding from light. After the reaction was completed, the plates were washed with T-PBS for three times. Antibody PY99 was added (100 µL/well), and the plates were shaked for 30 min at 37'C. After the reaction was completed, the plates were washed with T-PBS for three times. Horseradish peroxidase labeled sheep-against-rat IgG was added (100 µL/well), and the plates were shaked for 30 min at 37° C. After the reaction was complete, the plates were washed with T-PBS for three times. OPD developing liquid was added (100 µL/well), and reacted for 1-10 min at room temperature shielding from light. 50 µL of 2 M $H_2SO_4$ was added to quench the reaction. $A_{492}$ value was determined using wavelength-adjustable microplate reader VERSAmax.

The inhibition ratio of samples can be calculated by the following formula:

$$\text{inhibition ratio \%} = \left(1 - \frac{OD \text{ value of compound} - OD \text{ value of control without enzyme}}{OD \text{ value of negative control} - OD \text{ value of control without enzyme}}\right) \times 100\%$$

2. Results

| | % Inhibition ratio for tyrosine kinase at 10 µM | | |
|---|---|---|---|
| Compound No. | c-Kit mean value | PDGFR-β mean value | results |
| CM4306 | 80.6 | 85.8 | effective |
| CM4308 | 84.0 | 87.1 | effective |
| CM4309 | 85.2 | 88.2 | effective |
| Su11248 (positive drug) | 90.2 | 93.9 | effective |

The above results are the mean values for experiments in duplicate.

3. The Evaluation Standard and the Results

The compound has efficacy if the inhibition rate of the tested compound at the experimental concentration $10^{-5}$ mol/L was greater than 50%. The compound has no efficacy if the inhibition rate was less than 50%, provided that the inhibitory activity of the positive control compound meets the reference range.

The results showed that the inhibition ratios of CM4306, CM4308, CM4309 against protein tyrosine kinases c-Kit, PDGFR-β were more than 50%. Therefore, they had significantly inhibitory activity against c-Kit, PDGFR-β tyrosine kinase at the molecular level.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

What is claimed:

1. A method for preparing a salt of (methyl-d$_3$)amine, wherein, the method comprises:

reacting 2-(methyl-d$_3$)isoindoline-1,3-dione with hydrochloride acid to form (methyl-d$_3$)amine hydrochloride:

2. The method according to claim 1, wherein, the method comprises reacting 2-(methyl-d$_3$)isoindoline-1,3-dione with 6N hydrochloride acid:

3. An intermediate wherein, said intermediate is 2-(methyl-d$_3$)isoindoline-1,3-dione:

4. A process for preparing a compound having one of the following formula:

-continued

CM4307

CM4309 comprising reacting the compound of claim 3 with an appropriate precursor to form the specified compound.

* * * * *